United States Patent
James et al.

(10) Patent No.: US 10,617,555 B2
(45) Date of Patent: Apr. 14, 2020

(54) OSTOMY POUCH VENT AND METHOD OF VENTING AN OSTOMY POUCH

(71) Applicants: Aaron James, Grand Rapids, MI (US); Kellie Laine, Ada, MI (US)

(72) Inventors: Aaron James, Grand Rapids, MI (US); Kellie Laine, Ada, MI (US)

(*) Notice: Subject to any disclaimer, the term of this patent is extended or adjusted under 35 U.S.C. 154(b) by 453 days.

(21) Appl. No.: 15/434,547

(22) Filed: Feb. 16, 2017

(65) Prior Publication Data
US 2017/0239074 A1    Aug. 24, 2017

Related U.S. Application Data

(60) Provisional application No. 62/296,744, filed on Feb. 18, 2016.

(51) Int. Cl.
*A61F 5/441* (2006.01)
*A61F 5/445* (2006.01)

(52) U.S. Cl.
CPC .............. *A61F 5/441* (2013.01); *A61F 5/445* (2013.01); *A61F 2005/4415* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 4,268,286 | A | * | 5/1981 | Steer | A61F 5/441 55/385.4 |
| 4,296,749 | A | * | 10/1981 | Pontifex | A61F 5/445 604/344 |
| 4,411,659 | A | * | 10/1983 | Jensen | A61F 5/441 604/332 |
| 4,449,970 | A | * | 5/1984 | Bevan | A61F 5/441 55/385.4 |
| 4,451,258 | A | * | 5/1984 | Jensen | A61F 5/441 55/385.4 |

(Continued)

OTHER PUBLICATIONS

International Search Report of the International Searching Authority from corresponding Patent Cooperation Treaty (PCT) Application No. PCT/IB2017/050887, indicated completed on Apr. 23, 2017.

(Continued)

*Primary Examiner* — Tatyana Zalukaeva
*Assistant Examiner* — Guy K Townsend
(74) *Attorney, Agent, or Firm* — Gardner, Linn, Burkhart & Ondersma LLP

(57) ABSTRACT

An ostomy pouch vent includes a venting portion and a closure portion. The venting portion includes a cylindrical vent body defining a through-opening passage though the body. The closure portion including a closer body that is adapted to engage the vent body to selectively close the through-opening and a support member supporting the closure body. The support member manipulates the closure body into registration with the vent body to close the through-opening and manipulating the closure body away from the vent body to open the through-opening. A pair of grasping members extends in generally opposite directions from the support member. The grasping members have a grasping surface configured to be engaged by fingers of a user to apply a force to the support member.

19 Claims, 2 Drawing Sheets

(56) References Cited

U.S. PATENT DOCUMENTS

| | | | | |
|---|---|---|---|---|
| 4,479,818 | A | * | 10/1984 | Briggs .................... A61F 5/441 55/385.4 |
| 4,516,974 | A | * | 5/1985 | Davis ..................... A61F 5/441 55/385.4 |
| 4,668,258 | A | * | 5/1987 | Steer ....................... A61F 5/441 96/12 |
| 4,723,951 | A | * | 2/1988 | Steer ....................... A61F 5/441 55/505 |
| 4,938,749 | A | * | 7/1990 | Jensen .................... A61F 5/441 55/385.4 |
| 4,940,461 | A | * | 7/1990 | Steer ....................... A61F 5/441 55/385.4 |
| 4,941,869 | A |   | 7/1990 | D'Amico |
| 5,085,652 | A | * | 2/1992 | Johnsen .................. A61F 5/441 604/333 |
| 5,167,650 | A | * | 12/1992 | Johnsen ........... A61B 17/32053 604/332 |
| 5,593,397 | A |   | 1/1997 | La Gro |
| 5,626,569 | A | * | 5/1997 | Holtermann ............ A61F 5/441 251/262 |
| 5,658,266 | A |   | 8/1997 | Colacello et al. |
| 5,658,267 | A |   | 8/1997 | Colacello et al. |
| 5,683,372 | A |   | 11/1997 | Colacello et al. |
| 5,690,621 | A | * | 11/1997 | Canela .................. A61F 5/4407 604/333 |
| 5,733,271 | A | * | 3/1998 | Bjørn ....................... A61F 5/441 604/333 |
| 5,771,590 | A |   | 6/1998 | Colacello et al. |
| 5,840,073 | A | * | 11/1998 | Olsen ...................... A61F 5/441 604/333 |
| 5,947,941 | A |   | 9/1999 | Leise, Jr. et al. |
| 6,015,399 | A | * | 1/2000 | Mracna ................... A61F 5/445 604/332 |
| 6,709,421 | B1 | * | 3/2004 | Falconer ................. A61F 5/441 604/335 |
| 7,344,521 | B2 | * | 3/2008 | Andersen .............. A61F 5/4404 604/327 |
| 7,468,056 | B2 | * | 12/2008 | Burt ...................... A61F 5/4405 604/317 |
| 2002/0077611 | A1 | * | 6/2002 | von Dyck ............... A61F 5/442 604/333 |
| 2004/0024363 | A1 | * | 2/2004 | Goldberg ............ A61J 15/0015 604/175 |
| 2008/0275410 | A1 | * | 11/2008 | Burt ...................... A61F 5/4405 604/333 |
| 2009/0047890 | A1 | * | 2/2009 | Yano .................... B65D 77/225 454/143 |
| 2017/0239074 | A1 | * | 8/2017 | Mracna ................... A61F 5/441 |
| 2017/0360592 | A1 | * | 12/2017 | Carrubba ................ A61F 5/445 |

OTHER PUBLICATIONS

Written Opinion of the International Searching Authority from corresponding Patent Cooperation Treaty (PCT) Application No. PCT/IB2017/050887, indicated completed on Apr. 23, 2017.

* cited by examiner

OSTOMY POUCH VENT AND METHOD OF VENTING AN OSTOMY POUCH

CROSS REFERENCE TO RELATED APPLICATIONS

This application claims priority from U.S. patent application Ser. No. 62/296,744, filed on Feb. 18, 2016, the disclosure of which is hereby incorporated herein by reference.

BACKGROUND OF THE INVENTION

The present invention is directed to an ostomy pouch vent, a method of venting an ostomy pouch, and a vented ostomy pouch.

In commonly assigned U.S. Pat. No. 6,015,399, the disclosure of which is hereby incorporated herein by reference in its entirety, a vented colostomy pouch is disclosed that overcomes the problem of an accumulation of gas within the pouch, which inflates the pouch in an undesirable manner and may cause leakage or even rupture of the colostomy pouch. While the vented colostomy pouch in the '399 patent provided an important advancement in ostomy pouch design, it was not without its drawbacks.

SUMMARY OF THE INVENTION

The ostomy pouch disclosed in the '399 patent is used by ostomy patients of all ages and dexterity levels. Indeed, ostomy pouches are used from pre-school children up to nursing home patients. Those with limited dexterity may find it difficult to open the vent aperture in order to vent the pouch. The embodiments of the present invention are intended to provide an ostomy pouch vent, method of venting an ostomy pouch vent and a vented ostomy pouch that is reliably sealed yet can be easily opened for venting even by those of limited dexterity.

An ostomy pouch vent, according to an aspect of the invention, includes a venting portion and a closure portion. The venting portion includes a cylindrical vent body defining a through-opening passage though the body. The closure portion includes a closure body that is adapted to engage the vent body to selectively close the through-opening and a support member supporting the closure body. The support member manipulates the closure body into registration with the vent body to close the through-opening and manipulates the closure body away from the vent body to open the through-opening. A pair of grasping members extends in generally opposite directions from the support member. The grasping members have a grasping surface configured to be engaged by fingers of a user to apply a force to the support member.

The attachment member may have a first surface generally around the vent body and an adhesion surface opposite the first surface. The grasping members may be pivotable with respect to the support member. The grasping members may extend from the support member a greater distance than a separation between the support member and the attachment member when the closure body is engaging the vent body. In this manner, the grasping members engage the first surface when compressed together in order to apply a force in a direction tending to separate the support member from the attachment member. The grasping members may connect with the support member with a living hinge.

The grasping surface may include frictional members to increase friction between the grasping surface and the fingers of the user. The frictional members may include a plurality of ridges extending generally parallel the support member when the grasping members are moved with respect to the support member. A flexible tether may connect the support member with the attachment member. The attachment member and the tether may be formed as a generally planar member when the closure body is not engaging the vent body. A spacer may be attached to the support member or the attachment member, the spacer separating the support member and the attachment member when the closure body is engaging the vent body. The vent body may define a generally cylindrical inner surface, and the closure body may have an outer surface configured to engage the inner surface of the vent body.

An ostomy pouch vent, according to an aspect of the invention, includes a generally planar flexible member having an attachment portion, an opposite support portion and a tether portion between the attachment portion and the support portion. A cylindrical vent body extends from a first surface of the flexible member at the attachment portion and defines a through-opening passage though the flexible member. A second surface opposite the first surface has an adhesive thereon adapted to engage a surface of an ostomy pouch. A closure body that is adapted to selectively closing the through-opening extends from the first surface of the flexible member at the support portion. The closure body engages the vent body to close the through-opening when the planar flexible member is bent at the tether portion. The generally planar flexible member defines a pair of wing-shaped grasping members extending in opposite directions from the support portion. The pair of wings define a grasping surface engaged by fingers of a user to apply a force to the support member.

A method of venting an ostomy pouch made up of a pouch wall, according to an aspect of the invention, starts with a generally planar flexible member with a venting portion having a cylindrical vent body extending from a first surface of the planar flexible member defining a through-opening passage though the ostomy pouch wall, a closure support portion opposite the vent body and a tether portion between the venting portion and the closure support portion, the closure support portion having a closure body that is adapted to selectively close the through-opening extending from the first surface of the planar flexible member and a pair of wing-shaped grasping members extending in generally opposite directions from the support portion and wherein the closure body engages the vent body to close the through-opening when the planar flexible member is folded at the tether portion. The planar flexible members are grasped in order to apply a force to the support portion to separate the closure body from the vent body to vent the ostomy pouch.

The grasping members may extend from the support member a greater distance than separation between portions of the planar flexible member at the closure support portion and the venting portion when the closure body is engaging the vent body. The grasping may include squeezing the grasping members together until the grasping members engage the support member in order to apply a force in a direction tending to apply the force to the support member.

An ostomy pouch, according to an aspect of the invention, includes an ostomy pouch bag having a bag wall and a venting member attached to the bag. The venting member includes a cylindrical vent body defining a through-opening passage though the bag wall. A closure portion includes a closer body that is adapted to selectively closing the through-opening and a support member supporting the closure body. The support member manipulates the closure body into registration with the vent body to close the through-opening and manipulates the closure body away from the vent body to open the through-opening. A pair of grasping members extend in generally opposite directions from the support member, the grasping members have a grasping surface adapted to be engaged by fingers of a user to apply a force to the support member.

These and other objects, advantages and features of this invention will become apparent upon review of the following specification in conjunction with the drawings.

DESCRIPTION OF THE PREFERRED EMBODIMENT

Figure 1:
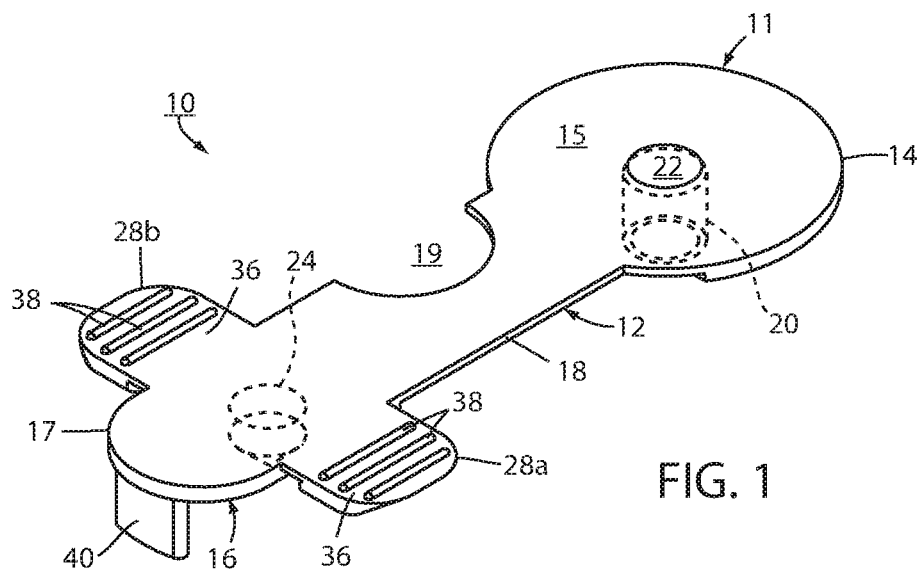
FIG. 1 is a perspective view of an ostomy pouch vent taken from the top side facing the ostomy pouch, according to an embodiment of the invention, in an open, venting orientation.
Figure 2:
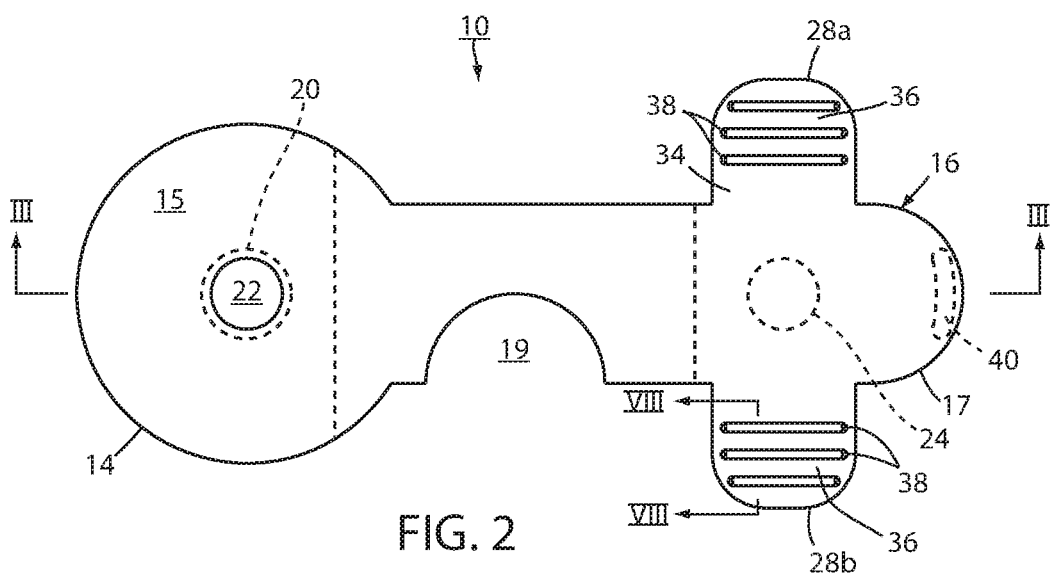
FIG. 2 is a top plan view of the ostomy pouch vent in FIG. 1.
Figure 3:
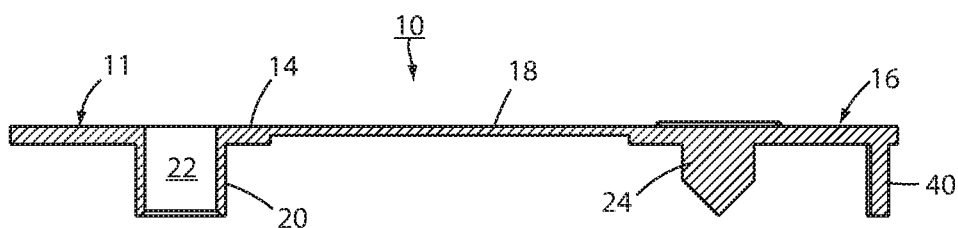
FIG. 3 is a sectional view taken along the lines III-III in FIG. 2.
Figure 5:
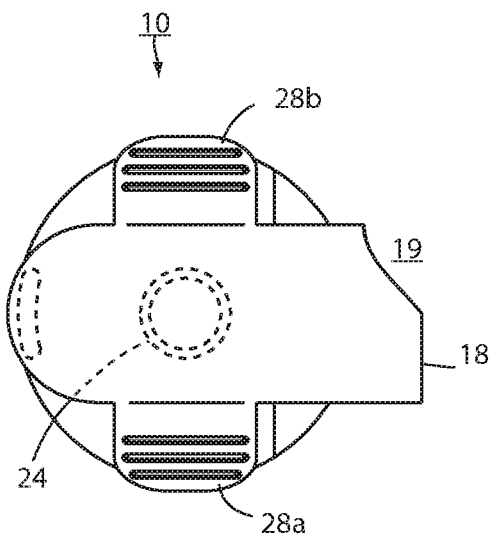
FIG. 5 is a top plan view of the ostomy pouch vent in FIG. 4.
Figure 6:
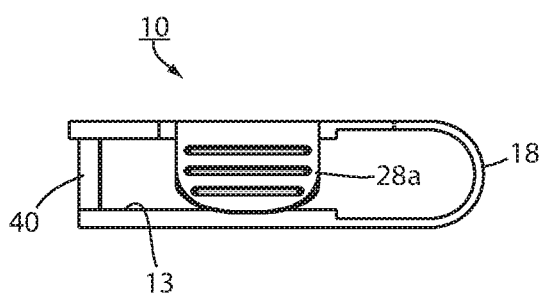
FIG. 6 is a side elevation view of the ostomy pouch vent in FIG. 4.

Referring now to the drawings and the illustrative embodiments depicted therein, an ostomy pouch vent 10 includes a venting portion 11 including a cylindrical vent body 20 defining a through-opening 22 passage though body 10 and through an opening in the wall of an ostomy pouch (not shown) in order to selectively vent the pouch of built-up gas. A closure portion 16 includes a closer body 24 that is adapted to engage vent body 20 to selectively close through-opening 22 and a support member 17 supporting closure body 24. Support member 17 manipulates closure body 24 into registration with vent body 20 to close through-opening 22 in the orientation shown in FIGS. 5-7. Support member 17 manipulates closure body 24 away from vent body 20 to open the through-opening as seen in the orientation shown in FIGS. 1-3. A pair of grasping members 28a, 28b extend in generally opposite directions from support member 17. Grasping members 28a, 28b have a grasping surface 36 configured to be engaged by fingers of a user to apply a force to support member 17 in a manner that will be explained below. While grasping members 28a, 28b may have some use in manipulating closure body 24 into registration with vent body 20, they are primarily functional in separating closure body 24 from vent body 20.

While it would be possible to mount vent body 20 directly to a wall of the ostomy pouch when marketed to the user, in the illustrated embodiment, the ostomy pouch vent 10 is a separate item that can be mounted to an ostomy pouch after market. As such, vent body 20 is mounted to an attachment member 14 having a first surface 13 that is generally around vent body 20 and an adhesion surface 15 opposite first surface 13. Adhesion surface 15 is adapted to adhering to the outer wall of an ostomy pouch, such as with an adhesive material applied to the adhesion surface. In the illustrated embodiment, pouch vent 10 is formed on a generally planar flexible member 12 that defines attachment member 14 and support member 17. Planar flexible member 12 additionally defines a tether portion 18 connecting attachment member 14 with support member 17. Tether portion 18 includes cut-out 19 in order to increase flexibility of the tether portion which is folded in order to engage closure body 24 with vent body 20. In the illustrated embodiment, vent body 20 defines a generally cylindrical inner surface and closure body 24 is in the form of a plug having an outer surface configured to engage the inner surface of vent body 20. However, it could, alternatively, be a cap that fits over an inner surface of vent body 20.

Figure 4:
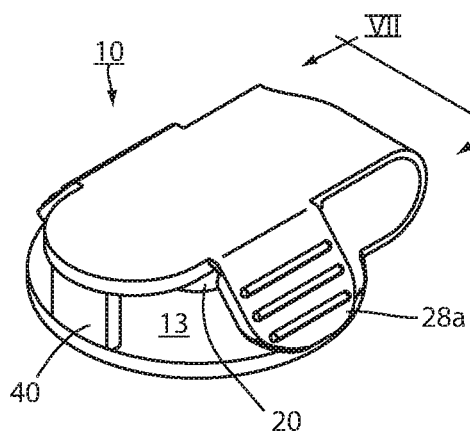
FIG. 4 is a perspective view of the ostomy pouch vent in FIG. 1 in a closed non-venting orientation.
Figure 7:
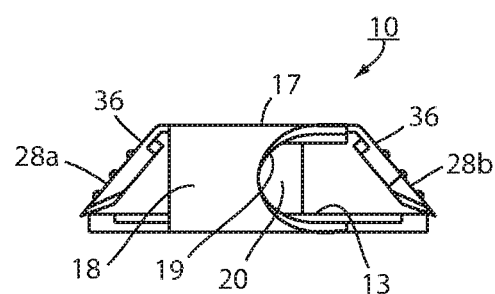
FIG. 7 is an end elevation view of the ostomy pouch vent in FIG. 4 taken from the direction VII-VII.
Figure 8:
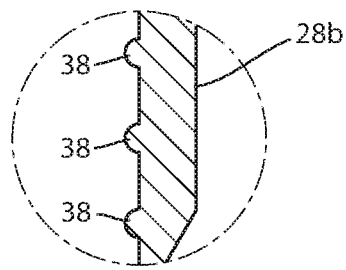
FIG. 8 is an enlarged sectional view taken along the lines VIII-VIII in FIG. 2.

Grasping members 28a, 28b are pivotable in the illustrated embodiment with respect to support member 17 so that they can be pivoted toward each other, as seen in FIG. 7. Each grasping member includes a grasping surface 36 to allow the user to squeeze the grasping members between the thumb and index finger to provide a greater hold of the support member. Also, grasping members 28a, 28b extend from support member 17 a greater distance than a separation between support member 17 and attachment member 14 when closure body 24 is engaging vent body 20, as best seen in FIGS. 4 and 7. This relative length causes grasping members 28a, 28b to engage the first surface 13 of attachment member 14 when the grasping members are compressed together in order to apply a force between the support member and the attachment member in a direction tending to separate the support member from the attachment member. Grasping members 28a, 28b are connected with support member 17 with living hinges 34 to provide for pivoting motion of the grasping members about the support member. Grasping surface 36 includes frictional members to increase friction between the grasping surface and the fingers of the user. In the illustrated embodiment, the frictional members include a plurality of ridges 38 extending generally parallel to the support member when the grasping members are pivotally moved with respect to the support member. Of course other frictional members may be provided. A spacer 40 is attached to support member 17, but could, alternatively, be attached to attachment member 14. Spacer 40 separates support member 17 from attachment member 14 when closure body 24 is engaging vent body 20. Spacer 40 restricts the engagement between the closure and vent bodies in order to ensure that the force of separation is not larger than necessary to provide an adequate closure of the vent opening.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. An ostomy pouch vent, comprising:
   a venting portion including a cylindrical vent body defining a through-opening passage through said body and a wall supporting said vent body;
   a closure portion including a closer body that is adapted to engage said vent body to selectively close said through-opening and a support member supporting said closure body, said support member manipulating said closure body into registration with said vent body to close said through-opening and manipulating said closure body away from said vent body to open said through-opening; and
   a pair of grasping members extending in generally opposite directions from said support member and pivotable with respect to said support member with a living hinge, said grasping members having a grasping surface configured to be engaged by fingers of a user to apply a force to said support member, wherein said grasping members extend from said support member a greater distance than separation between said support member and said wall when said closer body is engaging said vent body wherein a distal portion of said grasping members engage said wall when pivoted toward each other in order to apply a force between the support member and said wall to separate said closer body from said vent body.

2. The ostomy pouch vent as claimed in claim 1 wherein said venting portion includes an attachment member that surrounds said vent body, said attachment member having a first surface generally around said vent body and an adhesion surface opposite said first surface.

3. The ostomy pouch vent as claimed in claim 1 wherein said grasping surface includes frictional members to increase friction between the grasping surface and the fingers of the user.

4. The ostomy pouch vent as claimed in claim 3 wherein said frictional members comprise a plurality of ridges extending generally parallel the support member when said grasping members are pivoted with respect to said support member.

5. The ostomy pouch vent as claimed in claim 2 including a flexible tether connecting said support member with said attachment member.

6. The ostomy pouch vent as claimed in claim 5 wherein said support member, said attachment member and said tether are formed as a generally planar member when said closure body is not engaging said vent body.

7. The ostomy pouch vent as claimed in claim 1 including a spacer attached to said support member or said wall, said spacer separating said support member and said wall when said closure body is engaging said vent body.

8. The ostomy pouch vent as claimed in claim 1 wherein said vent body defines a generally cylindrical inner surface and said closure body has an outer surface configured to engage said inner surface of said vent body.

9. An ostomy pouch vent, comprising:
   a generally planar flexible member having an attachment portion, an opposite support portion and a tether portion between said attachment portion and said support portion;
   a cylindrical vent body extending from a first surface of said flexible member at said attachment portion and defining a through-opening passage though said flexible member, a second surface opposite said first surface at said attachment portion and having an adhesive thereon adapted to engaging a surface of an ostomy pouch;
   a closure body that is adapted to selectively close said through-opening extending from said first surface of said flexible member at said support portion wherein said closure body engages said vent body to close said through-opening when said planar flexible member is bent at said tether portion; and
   said generally planar flexible member defining a pair of wing-shaped grasping members extending in opposite directions from said support portion and pivotable with respect to said support portion with a living hinge, said grasping members defining grasping surfaces engaged by fingers of a user to apply a force to said support portion, wherein said grasping members extend from said support portion a greater distance than separation between said support portion and said attachment portion when said closure body is engaging said vent body wherein a distal portion of said grasping members engage said attachment portion when pivoted toward each other in order to apply a force between the support portion and said attachment portion to separate said closure body from said vent body.

10. The ostomy pouch vent as claimed in claim 9 wherein said grasping surface includes frictional members to increase friction between the grasping surface and the fingers of the user.

11. The ostomy pouch vent as claimed in claim 10 wherein said frictional members comprise a plurality of ridges extending generally parallel the support member when said grasping members are moved with respect to said support member.

12. The ostomy pouch vent as claimed in claim 9 including a spacer attached to said support member or said attachment member, said spacer separating said support member and said attachment member when said closure body is engaging said vent body.

13. The ostomy pouch vent as claimed in claim 9 wherein said vent body defines a generally cylindrical inner surface and said closure body has an outer surface configured to engage said inner surface of said vent body.

14. A method of venting an ostomy pouch made up of a pouch wall, said method comprising:
   providing a generally planar flexible member with a venting portion having a cylindrical vent body extending from a first surface of said planar flexible member and defining a through-opening passage though the ostomy pouch wall, a closure support portion opposite said vent body and a tether portion between said venting portion and said closure support portion, said closure support portion having a closure body that is adapted to selectively close said through-opening extending from said first surface of said planar flexible member and a pair of wing-shaped grasping members extending in generally opposite directions from said support portion and are pivotable with respect to said support portion with a living hinge and wherein said closure body engages said vent body to close said through-opening when said planar flexible member is folded at said tether portion; and
   pivoting said grasping members toward each other in order to apply a force to said support portion to separate said closure body from said vent body to vent the ostomy pouch, wherein said grasping members extend from said support portion a greater distance than separation between said support portion and said venting portion when said closure body is engaging said vent body wherein a distal portion of said grasping members engage said venting portion when pivoted toward each other in order to apply a force between the support portion and said venting portion to separate said closure body from said vent body.

15. The method as claimed in claim 14 wherein the venting portion is attached to an outer surface of the pouch with a second surface opposite said first surface of said flexible member.

16. The method of venting as claimed in claim 14 wherein said grasping surface includes frictional members to increase friction between the grasping surface and the fingers of the user.

17. The method of venting as claimed in claim 16 wherein said frictional members comprises a plurality of ridges extending generally parallel the support member when said grasping members are moved with respect to said support member.

18. The method of venting as claimed in claim 14 including a spacer attached to said planar flexible member at said closure support portion or said venting portion, said spacer separating end portions of said planar flexible member when said closure body is engaging said vent body.

19. An ostomy pouch, comprising:
an ostomy pouch bag having a bag wall;
a venting member attached to said bag wall, said venting member including a cylindrical vent body defining a through-opening passage though said bag wall;
a closure portion including a closer body that is adapted to selectively closing said through-opening and a support member supporting said closure body, said support member manipulating said closure body into registration with said vent body to close said through-opening and manipulating said closure body away from said vent body to open said through-opening; and
a pair of grasping members extending in generally opposite directions from said support member and pivotable with respect to said support member with a living hinge, said grasping members having a grasping surface adapted to be engaged by fingers of a user to apply a force to said support member wherein said grasping members extend from said support member a greater distance than separation between said support member and said bag wall when said closer body engages said vent body wherein a distal portion of said grasping members engage said bag wall when pivoted toward each other in order to apply a force between the support member and said bag wall to separate said closer body from said vent body.

* * * * *